US011861553B2

(12) United States Patent
Taylor

(10) Patent No.: US 11,861,553 B2
(45) Date of Patent: Jan. 2, 2024

(54) METHOD AND SYSTEM FOR DISINFECTING CONTENTS OF A SECURE LOCKABLE DELIVERY RECEPTACLE

(71) Applicant: Thomas Steven Taylor, Atlanta, GA (US)

(72) Inventor: Thomas Steven Taylor, Atlanta, GA (US)

( * ) Notice: Subject to any disclaimer, the term of this patent is extended or adjusted under 35 U.S.C. 154(b) by 321 days.

(21) Appl. No.: 17/371,445

(22) Filed: Jul. 9, 2021

(65) Prior Publication Data

US 2022/0012683 A1 Jan. 13, 2022

Related U.S. Application Data

(60) Provisional application No. 63/050,788, filed on Jul. 11, 2020.

(51) Int. Cl.
*G06Q 10/0836* (2023.01)
*G07C 9/00* (2020.01)

(52) U.S. Cl.
CPC ..... *G06Q 10/0836* (2013.01); *G07C 9/00182* (2013.01)

(58) Field of Classification Search
CPC .............................. G06Q 10/08; G06Q 10/083
See application file for complete search history.

(56) References Cited

U.S. PATENT DOCUMENTS 11,199,853 B1 * 12/2021 Afrouzi ................ G05D 1/0246
2005/0038685 A1 * 2/2005 Collins ............ G06Q 10/06398
705/332

(Continued)

FOREIGN PATENT DOCUMENTS

CN 111035161 A * 12/2019
WO WO-2017132482 A1 * 8/2017 ........... A47G 29/141

OTHER PUBLICATIONS

S.P. Deshmukha,b, S.M.Patila,c, S.B.Mullania, S.D.Delekara, Silver nanoparticlesasaneffective disinfectant:Areview, Materials Science &Engineering C 97 (2019) 954-965 , https://doi.org/10.1016/j.msec.2018.12.102 (Dec. 28, 2018). (Year: 2018).*

(Continued)

*Primary Examiner* — Emmett K. Walsh
*Assistant Examiner* — Larita L. Yusuf
(74) *Attorney, Agent, or Firm* — John L. Doughty; DOUGHTY LAW, L.L.C.

(57) ABSTRACT

A lockable package delivery locker at a publicly accessible location facilitates secure delivery by a delivery user of a package for later pickup by a recipient user. While the package is inside the locker a disinfection system disinfects the package and potentially its contents. A plurality of disinfection systems may provide different types of disinfection, including UV, chemical, nanotechnology, based on the type of packaging material. An electronic message may facilitate positioning UV emitters or chemical dispersion nozzles relative to the package. A locking mechanism and the disinfection system(s) may be controllable remotely from a server to which a computer device of the locker is in communication with, locally via an application on a UE device, or manually via an interface of the locker. The delivery user may be an individual shipping the package or a delivery service personnel, with the recipient user typically being the other.

19 Claims, 9 Drawing Sheets

(56) References Cited

U.S. PATENT DOCUMENTS

| | | | | |
|---|---|---|---|---|
| 2016/0216106 | A1* | 7/2016 | Motoyama | G07F 17/13 |
| 2017/0220996 | A1* | 8/2017 | High | G07C 9/33 |
| 2017/0287244 | A1* | 10/2017 | Jansen | A47G 29/141 |
| 2018/0300677 | A1* | 10/2018 | Wilkinson | G07C 9/00896 |
| 2019/0287063 | A1* | 9/2019 | Skaaksrud | G07C 9/00571 |
| 2020/0187694 | A1* | 6/2020 | Santangeli | G07C 9/00309 |
| 2021/0220498 | A1* | 7/2021 | Kashi | A61L 2/10 |

OTHER PUBLICATIONS

Smiota, Smart Lockers Provide Safe, Contactless Delivery to Help Stop the Spread of Pathogens—Smiota https://smiota.com/resources/smart-lockers-provide-safe-contactless-delivery-to-help-stop-the-spread-of-pathogens/ (Year: 2020).*

* cited by examiner

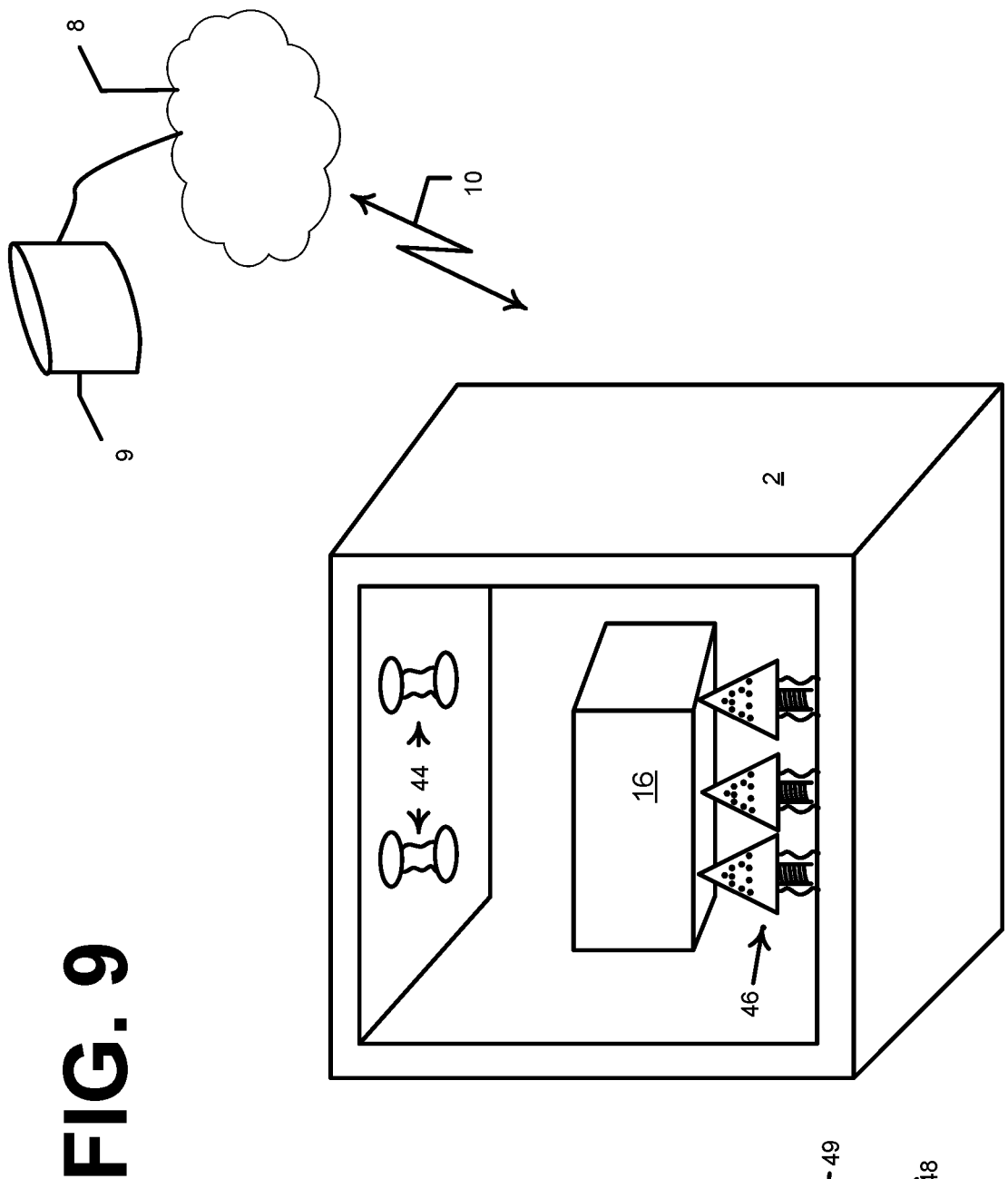
FIG. 9
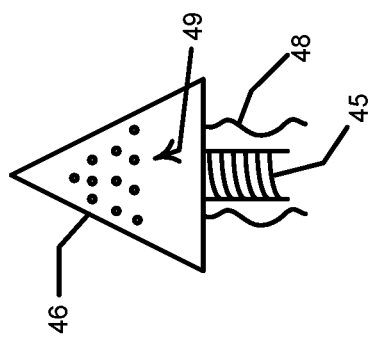

METHOD AND SYSTEM FOR DISINFECTING CONTENTS OF A SECURE LOCKABLE DELIVERY RECEPTACLE

CROSS REFERENCE TO RELATED APPLICATION

This application claims priority under 35 U.S.C. 119(e) to U.S. provisional patent application No. 63/050,788 "Shared delivery locker with a disinfection system," which was filed Jul. 11, 2020, and which is incorporated herein by reference in its entirety.

FIELD

The present invention relates to distribution of delivery items, and more particularly to the decontamination or disinfection of delivered packages that have been delivered to a secure compartment, or locker, for retrieval by authorized persons, machines, or devices.

SUMMARY

As commerce is moving to a web-based shopping experience, more and more shoppers are moving to on-line shopping. Many of these shoppers do not have their own secure way to receive the delivered goods. Individual shipping companies can no longer afford to have their own branded locker systems. As global pandemics grow, the need for disinfection and sterilization of shipped goods is increasing and is being applied before the recipient handles the shipped package. This Shared Delivery Locker with an Internal Disinfection Systems solves these problems.

A delivery locker can be used by many different delivery companies and can be shared by many different recipients. Each delivery locker has a Data Cloud-controlled locking mechanism that can be opened by the specific delivery company and the specific recipient for only a specific given-time. Each delivery locker contains a disinfection system to kill any contaminates such as viruses. The disinfection system can be light, chemical or nanotechnology based. The specific recipient gets a message with a specific unlock code that is only valued for a certain time and is only available for a time after the disinfecting is complete.

A method and a system are described. A system comprises a locker defining a cavity having one or more inner wall surfaces configured to contain delivery packages. The locker may be part of a plurality of lockers placed in an area that is accessible by a delivery service vehicle such as operated by the United States Postal Service, United Parcel Service, Inc., Federal Express, Inc., etc. The locker, or lockers, may be located where people tend to congregate, such as a grocery store, a household goods retail store, a gas station or electric vehicle charging station, and the like. A lockable door, that may be hinged, may be slidable, foldable, etc., includes a locking mechanism that may unlock in response to an electronic access request signal, which may be generated by a user's manual input to a locking mechanism interface, such as a touchscreen, a keypad, a mechanical combination lock wheel, and the like. The lockable door provides access to the locker cavity when the locking mechanism is unlocked and the door is moved from a closed position to an open position.

A disinfection system is located in or on the lockable package delivery locker. The disinfection system may be configured to disinfect contents contained in the cavity, such as a package that has been placed into the locker by a delivery user, such as a driver for a delivery service company. The disinfection system may comprise one or more of a plurality of types of disinfection systems that provide different types of infection, such as light/UV light/radiation, chemical, or nanotechnology material. The locker may include a computer system that includes a processor to process one or more electronic access request signals. The computer system may be coupled to, or part of a device that includes, the locking mechanism interface that can receive unlock information and unlock in response thereto. The processor may be configured to evaluate at least one identifier contained in the electronic access request signal to determine whether to provide an unlock message signal to the lockable door locking mechanism based on the evaluated identifier. The processor may be configured to determine whether the evaluation of the identifier contained in the electronic access request signal meets a predetermined unlock criterion, and provide an unlock message signal to the lockable door locking mechanism when the identifier contained in the electronic access request signal meets the predetermined unlock criterion.

The processor of the system may be further configured to evaluate the at least one identifier contained in the electronic request signal to determine a type of requestor that requested access to the cavity via the electronic access request signal. Examples of the type of requestor include a delivery user, such as a delivery service vehicle operator, a recipient user who may be an intended recipient of a package that is placed into the locker cavity before disinfection, a law enforcement personnel user, a system maintenance personnel user, and other personnel users who may have a need to access the inside of the locker according to rules promulgated by an operator entity that operates the disinfection locker or that operates a computer server that is configured to communicate with the locker via an electronic communication link, that may be a long range wireless link, a short range wireless link, or a wired communication link.

In an aspect the processor of the locker may be configured to provide a disinfect, or disinfection, signal to the one or more disinfection system(s) based on the type of requestor that requested access to the cavity via the electronic access request signal identifier and wherein the disinfection system performs a disinfection method to disinfect contents in the cavity after receiving the disinfect signal. In an aspect, the server provides the disinfection signal based on the requestor of the unlock information. The disinfection method can also be determined automatically based on the type of package or other parameters.

In an aspect, the system further comprises at least one contents sensor that is configured to sense characteristics such as material, size, shape, color, a barcode or QR code label, or location of a package within the cavity of the locker. The contents sensor, or sensors, may generate a contents-present signal, or a contents information signal that provides information corresponding to sensed characteristics, when a delivery package is inside the cavity. In the aspect, the processor may be further configured to receive the contents present signal or characteristics signal from the at least one contents sensor, provide a disinfect signal to the disinfection system based on the receiving of the contents present signal, or based upon the receiving of a contents characteristics signal, indicating the presence of contents in the cavity, or indicating characteristics of the package, respectively, and wherein the disinfection system performs a disinfection method to disinfect contents in the cavity after receiving the disinfect signal. The disinfection system type(s) and intensity level(s) may be selected based on information contained in the presence or characteristics signal(s).

In an aspect, the lockable door defines an outside and an inside. The disinfection system may be further configured to disinfect the inside of the lockable door and the inner wall surfaces of the cavity in response to receiving a disinfect signal when the content-present signal indicates that contents are not present in the cavity of the locker. This aspect may be used for maintenance or routine cleaning purposes.

In an aspect, the electronic access request signal may be transmitted via a cellular wireless signal, a Bluetooth wireless signal, or an internet-based connection by an application program interface running on, hosted by, or in communication with a cloud-based computer server. In such a scenario, the cloud-based server may communicate electronically with a user, such as a delivery user or a recipient user, via an application running on a User Equipment ("UE") device of the user, such as, a cellular mobile smart phone, a wireless connected tablet, a laptop computer, a smart watch, other wearables, and the like. Examples of the application may be SMS messaging, Facebook Messenger, e-mail, or the like.

In an aspect, the electronic access request signal may be transmitted via a cellular wireless signal, a Bluetooth wireless signal, from an application program interface running on a delivery user's UE device.

In an aspect, the disinfection system emits light within the cavity of the locked locker (door closed and locked) to kill germs, bacteria, mold, fungus, viruses, or other pathogens.

In an aspect the disinfection system sprays, fogs, discharges liquid, drizzles, or otherwise introduces one or more chemicals into the cavity of the locked locker to kill germs, bacteria, mold, fungus, viruses, or other pathogens.

In an aspect the disinfection system subjects contents contained within the cavity to nanotechnology materials to kill germs, bacteria, mold, fungus, viruses, or other pathogens.

In an aspect, a disinfection locker system service provider server comprises a processor configured to receive a locker access request message from a user, which may be a delivery user, a recipient user, maintenance user, or operator user, to access the inside of an electronically lockable package delivery locker. The server generates unlock information (delivery, recipient, maintenance, operation, etc.) and sends the unlock information in an unlock message signal (delivery, recipient, maintenance, operation, etc.) to a UE device of the user. The server receives a message from the lockable package delivery locker that the unlock information transmitted in the unlock message signal was used to unlock the lockable delivery locker, The server sends a confirmation message to a UE of the user that the lockable package delivery locker was unlocked using the unlock information. If the unlock request was for delivery unlock information, the server may receive a message from the lockable package delivery locker that a disinfection system began disinfection inside the lockable package delivery locker. The server may send a confirmation message to the delivery user's UE (if the unlock information sent was delivery unlock information; if the unlock information was maintenance unlock information; or if the unlock information was operation unlock information; (essentially not recipient unlock information)) that the disinfection began inside the lockable package delivery locker. The server may receive a message from the lockable package delivery locker that the disinfection inside the locker completed, send a message to the delivery (or maintenance or operation) user's UE that the disinfection inside the lockable package delivery locker completed, and send a recipient unlock message containing recipient unlock information to a UE of a recipient user but not to the UE of the delivery user (or maintenance or operation user), wherein the recipient unlock information is different from the delivery (or maintenance or operation) unlock information.

In an aspect, the processor of the server may be further configured to receive a contents-locked message signal that includes information indicating that a door of the lockable package delivery locker has been closed and locked after the message was received from the lockable package delivery locker that the delivery unlock information transmitted in a delivery unlock message signal was used to unlock the lockable package delivery locker and wherein the disinfection system does not begin the disinfection of the inside of the lockable package delivery locker until after the transmitting of the contents-locked message signal by the lockable package delivery locker. The contents-locked message signal may be referred to as a contents-inside-door-locked message signal. It will be appreciated that one of the purposes of this aspect is to ensure that one or more disinfection system do not begin disinfecting a package until the locker has been locked with a package contained there. In a maintenance or operation scenario, the aspect would not need to have a package contained in the locker before disinfection begins when the purpose of the disinfection is to clean or disinfect the inside of the locker itself.

In an aspect, a processor of the server may be further configured to transmit to the lockable package delivery locker disinfection type information based on a type of packaging used for the package, wherein the disinfection type information is intended to be used by the disinfection system to select a type of disinfection to use for disinfecting the package. In the aspect, the disinfection locker system service provider server contains information the corresponds to the type of packaging used for the package. For example, if a shipper of the package conveys to the server upon initiating the shipping of a package to a recipient a type of material used for the package, the server would possess information that could be used to instruct the locker which of multiple types of disinfection to use. For example, if the package is made from uncoated cardboard, UV light may be a preferred disinfection method if a liquid chemical would weaken the cardboard packaging material. If the packaging material is plastic, a chemical disinfection process may be more appropriate. It will be appreciated that a chemical or nanotechnology disinfection process may include rinsing a package with clean water after chemical disinfection chemical has been applied to the package.

In an aspect, a method comprises unlocking a lockable package delivery locker using recipient unlock information, wherein a disinfection system performs a disinfection process inside the lockable package delivery locker after a delivery user used delivery unlock information to gain access to the inside of the lockable package delivery locker and deliver the package into the lockable package delivery locker and before the recipient unlock information was requested. This aspect highlights action performed by a recipient user wherein the recipient user is retrieving a package from a lockable package delivery locker after a disinfection system has applied a disinfection process to the package inside the locker.

In an aspect the recipient unlock information was requested using a UE device of a recipient user. The request may have been transmitted over a communication network to a server, or may have been transmitted to a computer device of the locker itself. The recipient UE may receive information, such as a random number or other unlock information that is shared with the locker computer device and the each of the locker computer device and the recipient UE device may calculate a value from the recipient unlock information that is then provided to the locker, either from the recipient UE or manually by the recipient user using an interface of the locker.

In an aspect the disinfection system is determined from among a plurality of disinfection systems corresponding to the lockable package delivery locker based on package information associated with the package. The package information may be provided by a disinfection locker system service provider server. The package information may be provided by a UE device of the delivery user. The package information may be provided by a computer device of the lockable package delivery locker.

In an aspect, a computer device of the lockable package delivery locker may determine the package information based on package sensor signals sent to the computer device of the lockable package delivery locker from package sensors configured to detect contents of the lockable package delivery locker.

In an aspect, the computer device of the lockable package delivery locker determines the package information based on package sensor signals sent to the computer device of the lockable package delivery locker from package sensors configured to detect a position of contents of the lockable package delivery locker. Thus, disinfection system(s) selection, intensity level(s) generally, or intensity level(s) for specific light/radiation emitters or chemical or nanotechnology nozzles may be based on the type of packaging, the contents of the package, or the position or the package inside the locker.

BRIEF DESCRIPTION OF THE DRAWINGS

FIG. 9 illustrates standoff nozzles used in a disinfection delivery locker 2.

DETAILED DESCRIPTION OF THE DRAWINGS

Figure 1:
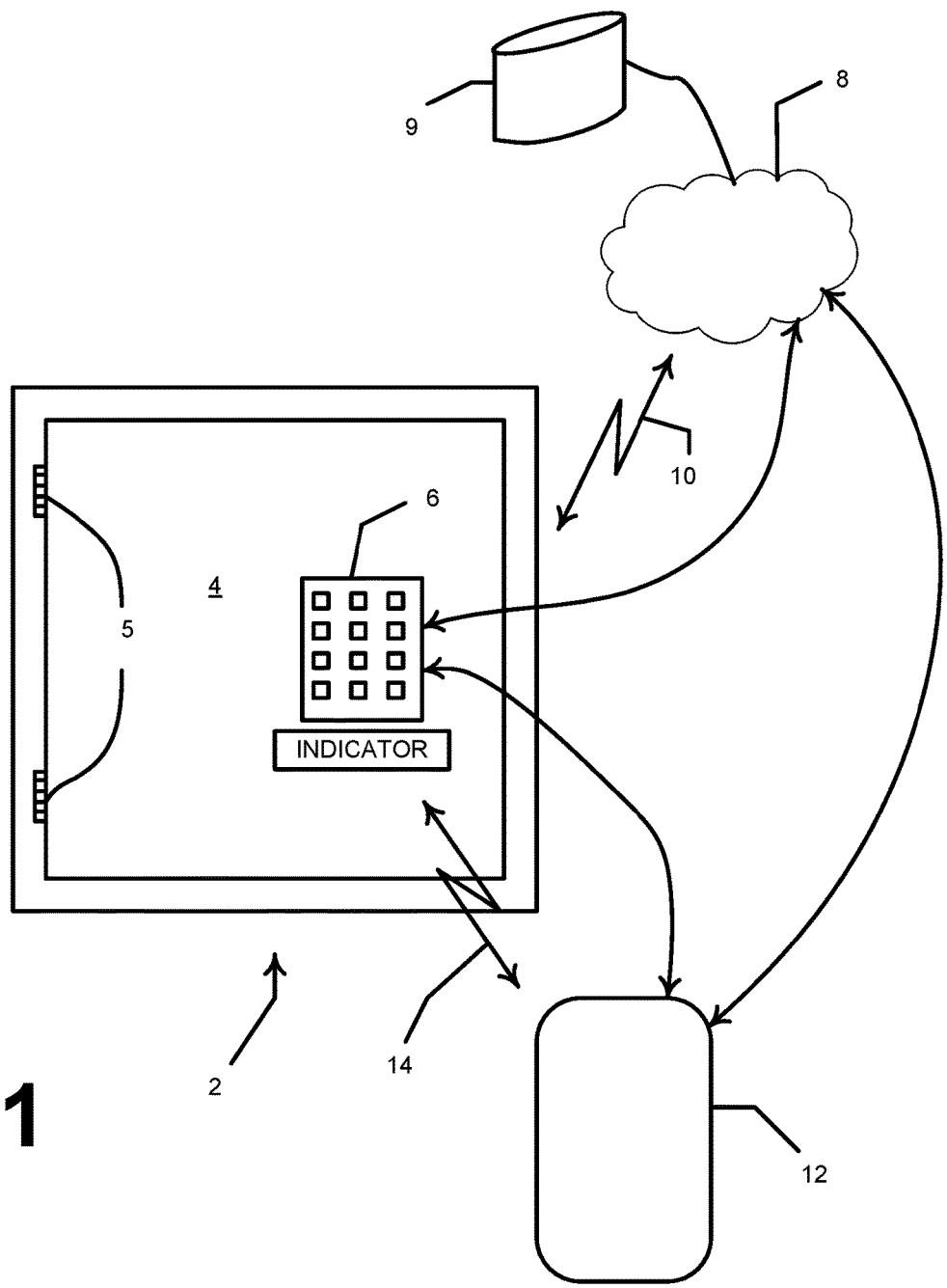
FIG. 1 illustrates a delivery locker with an internal compartment configured to receive and contain delivery packages.

As a preliminary matter, it will be readily understood by those persons skilled in the art that the present invention is susceptible of broad utility and application. Many methods, embodiments, and adaptations of the present invention other than those herein described as well as many variations, modifications and equivalent arrangements, will be apparent from or reasonably suggested by the substance or scope of the present invention.

Accordingly, while the present invention has been described herein in detail in relation to preferred embodiments, it is to be understood that this disclosure is only illustrative and exemplary of the present invention and is made merely for the purposes of providing a full and enabling disclosure of the invention. The following disclosure is not intended nor is to be construed to limit the present invention or otherwise exclude any such other embodiments, adaptations, variations, modifications and equivalent arrangements, the present invention being limited only by the claims appended hereto and the equivalents thereof.

A delivery locker, as disclosed herein, can be used by many different delivery companies and can be shared by many different recipients. A given delivery company establishes an account with a data-cloud-controlled locking system service provider. The data-cloud-controlled locking system service provider provides a protocol for unlocking an empty delivery locker. The protocol may include encryption credentials such as public/private keys, hash values, values used to create a hash of a unique shared value or values, and the like. The encryptions values and the shared value(s) may be stored in a subscriber identity module ("SIM") profile, which profile may be stored in a card that may be removed from a device, such as a SIM card that may be removably installed in a UE device. The encryption and shared values may be stored s part of a SIM profile stored in a soft SIM or in an eSIM.

A given locker door is usually locked. When a delivery company's delivery personnel arrives at a specific locker, the personnel unlocks the locker door using unique unlock information that is provided by the data-cloud-controlled locking system service provider. In an aspect, the delivery user may be a robot. The unique unlock information, which may include a code value, may be provided in an unlock information message to a UE in the possession of the delivery personnel via a wireless communication link such as cellular, Wi-Fi, Bluetooth, and the like. The same unlock information, for example a code value, is provided to the specific locker also by a wireless system such as cellular, Wi-Fi, Bluetooth, etc. The unlock information message may include an identifier of the specific locker, which may be physically marked with unique identifier that are visible to delivery personnel, so that the delivery personnel can physically identify which locker to unlock if there are a plurality of locked lockers located adjacent one another.

When the delivery personnel places a package to be delivered to a recipient in the locker and the door is lock, a disinfection system may begin a process of disinfecting contents of the locker. When the disinfection process begins a processor that controls the disinfection system may start a disinfection timer to determine when the package can be picked up by the recipient based on the type of packaging material used for the package and the type of disinfection mode that the disinfection system uses, which disinfection mode may be manually selected by the delivery personnel using an application running on the delivery person's UE, or the mode may be automatically selected, for example, based on a manually entered type of packaging material entered by the delivery personnel or based on an automatically sensed packaging type as the processor that controls the disinfection system may determine based on input signals received from one or more material type sensing sensors located in the housing, or container that defines the locker.

Typically, the shared locker will already have electrical power to control the locking mechanism. The power may be provided via an alternating current connection, such as 110V household current. Or, the power may be provided to the locker via a DC power supply such as batteries or a separate DC power supply.

When the new package has been placed in the locker and the disinfection system has begun the locker cannot be unlocked by the delivery persons or the package recipient. In an aspect, a master administration operation unlocking code may be used by a master administrator to unlock the locker in an emergency situation.

If the locker is not empty or has not been unlocked by a pervious recipient the delivery company will be prohibited from using that specific locker and they will be given unlock information for a different specific delivery locker, or they will manually select a different specific delivery locker.

It will be appreciated that delivery personnel may refer to a person employed by a delivery company that is delivering a package to the locker for pickup therefrom by an end-use/consumer who has ordered the contents of the package from a vendor who sent the package to the locker. Or, delivery personnel may refer to a consumer who has packaged an item to send to someone else, whether another individual or to a vendor, and who delivers the package to the locker for pickup by personnel employed by a delivery company, which employee in this scenario would be the recipient.

Each delivery locker has a Data Cloud-controlled locking mechanism that can be open by the specific delivery company and the specific recipient for only a specific given-time. The delivery company will only be able to unlock the specific locker during a specified short time frame. This is a time-based security protocol.

Each delivery locker contains a disinfection system to kill any contaminates on the package such as a virus. Either the delivery company or the recipient can select the delivery locker with the specified disinfection delivery system. There can be different pricing used for the different disinfection systems, that can be paid for by the delivery company, the recipient or both.

The disinfection system can be light, chemical or nanotechnology based. There are multiple disinfection systems can be used either solely or in combination with other systems. They fall into three major categories; light-based, chemical-based or nanotechnology-based. They each work using different virus killing methodologies.

The light-based systems typically use specific spectrums of light, often in the ultraviolet bands. These light band are known to kill various virus, typically in the time that a package may reside in delivery locker. The inner walls of the delivery locker will be made of such a material that they reflect these light bands very well, thus reaching all sides of the delivery package. This disinfection system only needs to have electrical power provided for the operation of the disinfection light. There can be a sensor in each locker to detect that light is on and the light level. This can be used as a part of the maintenance system to determine if the light should be replaced. If the light does not turn on, or the light level is low, the administrator will be notified by the wireless system to the Data Cloud. If the light fails to come on when the door is closed the delivery person will notified immediately and told to use another locker. The locker with the failed light will be taken off-line until the light situation is remedied and repaired.

The chemical-based systems are the most traditional way of killing various bacteria and viruses. The chemical is dispensed with an aerosol system to coat the outer surfaces of the delivery package, thus killing the bacteria or viruses that reside on the package. The chemical-based system will need a delivery system for the chemicals. This can be done with one storage tank of chemicals for an entire set or subset of lockers. The chemicals will be distributed with a simple pump system from the storage tank to each of the lockers. Each locker will have its own electrical-powered aerosol pump mechanism to distribute the chemicals onto the package. Each locker can have vents on the door, much like an old-style school locker. This will allow for air circulation and better distribution of the aerosol chemicals. The locker can also have an electrical fan than can be timed to come on at the optimal time to best distribute chemical disinfecting chemical. If the locker system does not allow for vents on the front door, a fan powered exhaust system can be used to pull in outside air and exhaust chemical vapor as required. There will be a chemical flow rate and pressure sensor to measure the flow and pressure of the chemicals being distributed. If any of the flow or pressure parameter are out of specification, when the door is closed the delivery person will notified immediately and told to use another locker. The locker with the failed aerosol system will be taken off-line until the situation is remedied and repaired.

The nanotechnology-based systems also use an aerosol system but using individual nanoparticle that attack individual viruses. Each individual nanoparticle can kill the virus through various methods, but as lacerating the virus. The nanotechnology-based system will need a delivery system for the nanotech substance. This can be done with one storage tank of the nanotechnology elements for an entire set or subset of lockers. The nanotech substance will be distributed with a simple pump system from the storage tank to each of the lockers. Each locker will have its own electrical-powered aerosol pump mechanism to distribute the nanotech substance onto the package. Each locker can have vents on the door, much like an old-style school locker. This will allow for air circulation and better distribution of the aerosol nanotech substance. The locker can also have an electrical fan than can be timed to come on at the optimal time to best distribute nanotech disinfecting substance. There will be a substance flow rate and pressure sensor to measure the flow and pressure of the nanotech substance being distributed. If any of the flow or pressure parameter are out of specification, when the door is closed the delivery person will notified immediately and told to use another locker. The locker with the failed aerosol system will be taken off-line until the situation is remedied and repaired.

Each locker is sealed so that if a virus in placed in the locker, potentially from being on a package, the virus cannot jump to adjacent lockers. It will be killed by the disinfection system so that it cannot contaminate other lockers, other packages or other people.

There can be a virus detection system in each locker. This detection system can use a machine-learning optical system that can detect known and new virus. This information can be sent to the Data Cloud to be used to continually update or improve the disinfection systems.

The Data Cloud can also be used with the virus detection system to generate virus mapping statistics such as: virus origination by geography, distribution and deliver company, size of package, type of packing material, time of day of delivery and other pertinent data.

Virus tracking system. As the sign-in from the delivery agent for the package delivery to the locker and the sign-in for the pickup of the package by the recipient, if the package is detected to have a virus, the virus contagion can be track backwards to the delivery company and their distribution system as well as forward to the recipient.

During the disinfection process time the specific recipient gets a message with a specific unlock code that is only valid for a certain time window and is only available for a time after the disinfecting is complete. Once the disinfection process is complete, the recipient with the proper unlock code can unlock the delivery locker and remove the now disinfected package.

Turning now to the figures, FIG. 1 illustrates a delivery locker 2 that may facilitate sharing an internal container for distributing delivery packages. Locker 2 is shown with a hinged, lockable door 5. In the figure door 4 is shown with hinges 5 external to the compartment the door defined by the door and the housing of locker 2; it will be appreciated that the hinges may be mounted internal to the compartment for security reasons. A locking mechanism of door 4 may be controlled, or locked/unlocked by entering a conde into keypad 6. The locking code, or unlocking code, may be a one-time-use code or may be a code to be used for multiple lock or unlock instance. The keypad may include a computer device that may include a wireless communication device, such as a cellular phone module, or wireless data modem, for communicating with a server 9, which may be a disinfection locker system service provider cloud server, coupled with data cloud 8 via wireless link 10. Wireless link 10 may be a short-range wireless link that communicates according to a wireless protocol, examples of which include Wi-Fi, Bluetooth, and the like. Wireless link may be a long-range wireless link, such as, for example, a cellular wireless link for communicating with a cellular wireless network such as a 3G, 4G, 5G, xG, LTE, CDMA, GSM, and similar network. The computer device associated with keypad 6 may include electronics similar to a common cellular wireless mobile phone or other wireless device such as a tablet. For purposes of discussion herein, a user's mobile phone/device may be referred to as a user equipment device ("UE") and the computer device associated with keypad 6 may be referred to herein generally as a wireless locking mechanism, although the circuitry and components (i.e., processor, memory, modem, GPS receiver module, etc.) may be similar. It will be appreciated that communication link 10 may be a wired communication link instead of a wireless link, such as an Ethernet communication link or similar. Door 4 may have an automatic opening or closing mechanism, such as a spring or a motorized plunger, such that a user's UE 12 in communication with keypad/computer device 6 via short range wireless link 14 (i.e., Bluetooth, or similar) can control hands-free opening and closing of the door.

Figure 2:
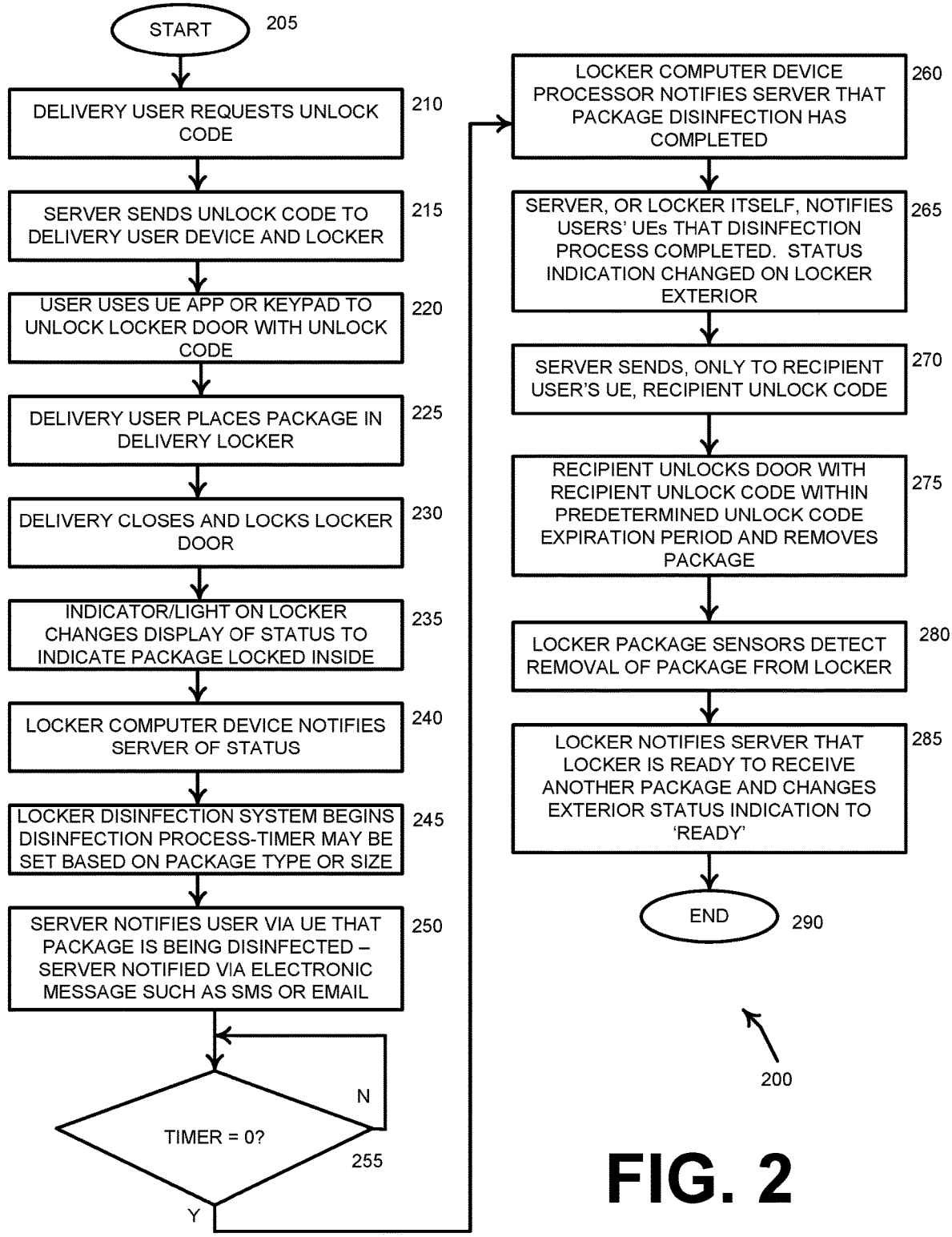
FIG. 2 illustrates a flow diagram of a method for facilitating the delivery of one or more packages via a lockable locker that is configured to perform a disinfection process on contents contained in the lockable locker.

Turning now to FIG. 2, the figure illustrates a flow diagram of a method 200 for facilitating the delivery of one or more packages via a lockable locker that is configured to perform a disinfection process on contents contained in the lockable locker. Method 200 starts at step 205. At step 210 a delivery personnel user requests an unlock code from a package delivery management server system, which may be represented as server 9 in FIG. 1. Continuing with discussion of FIG. 2, at step 215 the management server sends unlock information, which may include an unlock code, to a UE device of the delivery person and to the lockable locker. At step 220 the delivery user uses an application running on his or her UE device, or the user may use a keypad on the locker, to unlock the locker. A processor of the locker may receive unlock information, such as a code, from the user's UE device and compare it to the unlock information that it received after the server system transmitted the unlock information at step 215. At step 225 the delivery user places the package in the lockable locker. Step 230 the user closes and locks adore of the lockable locker. At step 235 a light, or other indication, on the locker's exterior, or near the locker, may indicate a changed status of the contents of the locker. For example, the indication may be a light that illuminates with the contents have been placed in the locker and that the locker has been locked. The locker notifies that server of the changed status at step 240.

At step 245 the locker begins a disinfection process. The disinfection process may include the setting of a timer wherein the timer is set based on the type of package that has been placed inside the locker at step 225. In addition, the type of disinfection may vary based on the type of package that has been placed in the lockable delivery locker. For example, if the exterior packaging material is carboard, the type of disinfection used may be ultraviolet ("UV") light. If the exterior packaging material is plastic, a chemical disinfection process may be used instead, or in addition to, UV light/radiation. If the contents being delivered are food items that are being delivered for immediate consumption without further cooking or heating, heater elements or UV elements may be activated to direct heat toward the food container. Or, chemical disinfection, for example using ethylene oxide, may be performed by fogging the interior of the locker using fogging nozzles that direct chemicals into the interior of the locker. Sensors inside the locker container may detect the type of packaging, or contents thereof, and automatically select a type of disinfection process based on the type of packaging or contents. Or, as illustrated in FIG. 1, a user's application, for example an application running on a smartphone, a personal computer, or a tablet, that is in communication with locker keypad 6 directly via wireless link 14 or may be indirectly in communication with keypad 6 via server 9 may be used to select a type of disinfection process to use. Or, based on detected packaging type or content type, server 9 may select a disinfection process type and send it to keypad 6, which may be configured to receive input received from UE 12, from server 9, or keys of the keypad, and control disinfection apparatuses, such as nozzles or UV radiation emitters, during a disinfection process.

Returning to discussion of FIG. 2, at step 250 the server notifies the user's, or users', UE device(s) that the disinfection process has begun. The users receiving such notification may include the delivery person who placed the package into the locker at step 225 and a recipient who will be retrieving the disinfected package from the locker.

At step 255 a processor of the locker determines whether the timer has elapsed. If not, method 200 returns to step 255. When the timer has counted down to zero/elapsed, method 200 advances to step 260.

At step 260 a processor of the locker notifies the server that package disinfection has completed. At step 265 the server or perhaps the locker itself notifies UE devices of users that the disinfection process has completed. Status change indication on the locker may be updated to indicate that the disinfection process has completed. For example, during the disinfection process a light may illuminate with a red color. When the process of disinfection has completed the status indication may change to indicate the disinfection process has completed (e.g., the light may change to green). At step 270 the server sends an unlock code only to a recipient of the package and to the locker. Unlike at step 250, where both the delivery personnel user and a recipient user may be notified that the disinfection process has begun, only the recipient user receives the unlock code at step 270. Thus, after the delivery person has placed a package in the locker at step 225 and locked the locker at step 230, only the intended recipient of the package can unlock the locker at step 275 to retrieve the package using the unlock code sent from the server at step 270. In an aspect, the recipient user must use the code within an expiration period or request a new code.

At step 280, sensors, which the locker may comprise, may sense the absence of the package that was previously contained in the locker at step 280 and send a locker empty message to the server at step 285, indicating that the locker is ready to receive another package, perhaps intended to retrieval by the same user who retrieved the package at step 275, or perhaps for a different intended recipient. A processor of the locker may update the status of the external indication (perhaps the light that is illuminated with a green color is changed to another color such as orange or is extinguished) to indicate that the locker is ready to receive another package. Method 200 ends at step 290.

Figure 3:
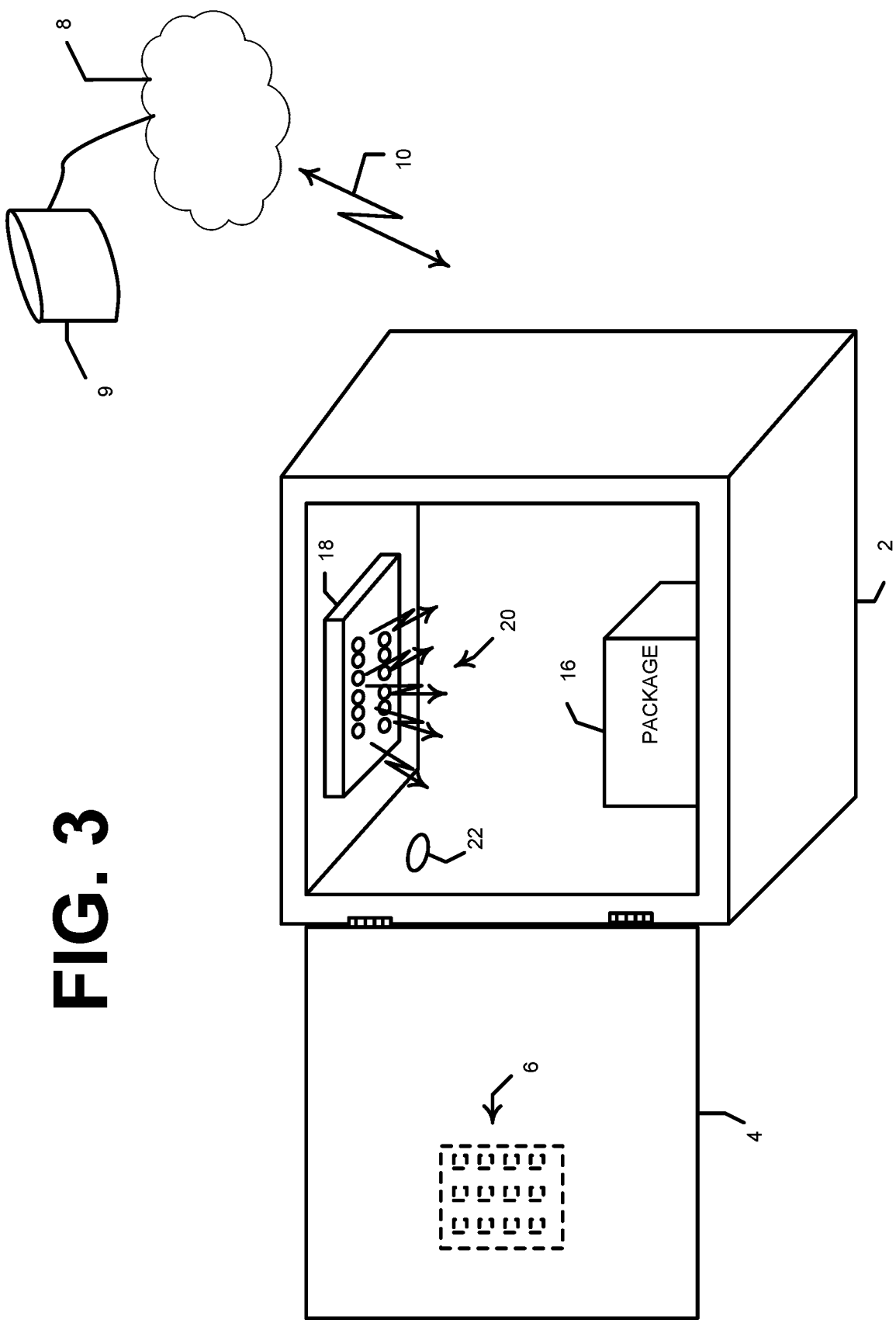
FIG. 3 illustrates a lockable locker with a light/radiation disinfection system.

Turning now to FIG. 3, the figure illustrates a lockable locker 2. Door 4 is shown in an open position and a backside of key pad 6 is shown. As discussed above in reference to FIG. 1, keypad 6 may include computer circuitry that may further include a data modem for communication via data link 10 and data clout network 8 with server 9. A package 16 is shown having been placed into a cavity of, or container defined by, locker 2. A light delivery system 18 is shown with rays of light radiation 20 emanating from the light delivery system. Light sensor 22 detects when light radiation 20 is emitted from system 18 and may provide an input signal to electronic circuitry of keypad/computer/device 6 for processing. For example, an external indication on locker 2 may comprise an LED capable of emitting different colors and may emit a red color when sensors 22 detect that light radiation is present inside of locker 2. It will be appreciated that radiation emitting system 18 may be configured to emit light in a visible spectrum, light in an ultraviolet spectrum, light in a subvisible spectrum, such as infrared, or heat. Radiation emitting system 18 may also be configured to emit ultrasonic sound waves that may effectuate disinfecting or sanitizing of the exterior of package 18 or contents contained therein.

Figure 4:
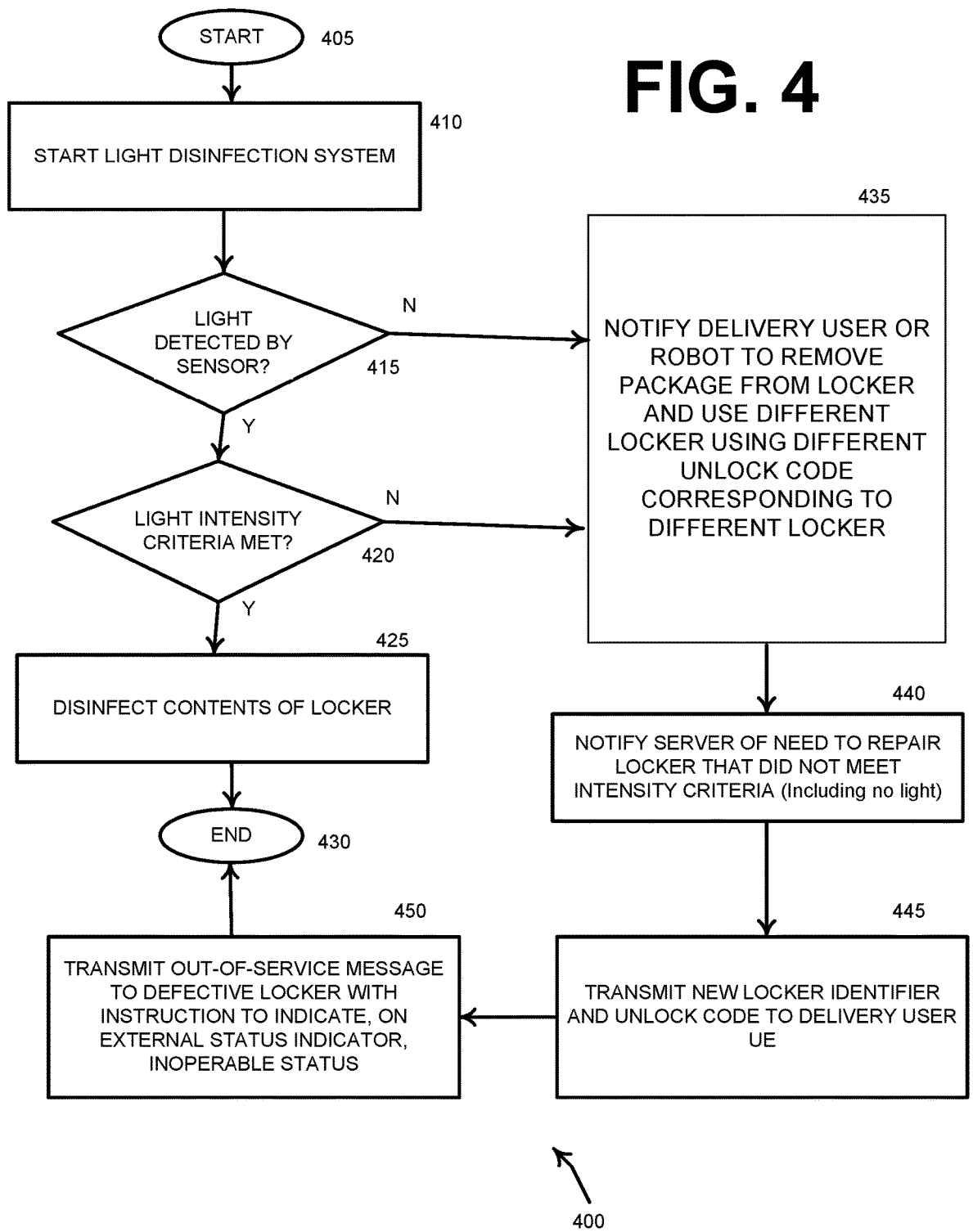
FIG. 4 illustrates a flow diagram of a light power disinfection and detection system process. A similar process may be used for chemical or nanotechnology material disinfection with modification as described in more detail below.

Turning now to FIG. 4, the figure illustrates a flow diagram of a light power disinfection and detection system process 400. Process 400 begins at step 405. At step 410 a computer program running on a computer device of a disinfection locker begins the emitting of disinfecting light/radiation at step 410. In an aspect, instead of running locally on a computer device of the disinfection locker, the computer program may be running on a remote server that provides instruction via a data communication link to a device that locally controls the locker and disinfection system thereof. The emitting of radiation that begins at step 410 may include the emission of light radiation from a light emitting system inside of a locker. The light emitted may be visible light, ultraviolet light, infrared light, or another type of radiation or wave that may facilitate disinfection of contents of the locker according to an instruction received either from a locker management server, a user equipment device of a delivery person or a recipient person located near the locker, or an input device of the locker, such as keypad 6 shown in figures described elsewhere herein. At step 415 the computer program determines whether light or other radiation is detected by a light/radiation sensor. If light or other radiation as the case may be is detected, process 400 advances to step 420. At step 420 the computer program determines whether a light intensity level value as provided in a light intensity message signal by the light sensor at step 415 meets a predetermined light intensity level criteria. The predetermined light intensity criteria may be stored in the computer program, may be generated in response to a package size value as provided from a delivery user using his, or her, US device, may be provided from a package delivery/disinfection management server, or manually via an input using keypad 6 as shown in figures described elsewhere herein.

If the light intensity detected by the light sensor inside the locker meets predetermined intensity criteria, process 400 advances to step 425. At step 425 radiation emitting system that emits disinfecting radiation inside the locker continues to produce radiation to disinfect contents of the locker for a predetermined period that may be based upon the type of package and contents contained in the locker. Process 400 ends at step 430.

Returning to discussion of step 415, if a light/radiation sensor that is configured to detect light/radiation inside of the disinfection locker does not detect the presence of light after the emission system should have begun emitting the light/radiation, process 400 advances to step 435.

Returning to discussion of step 415, if a light/radiation sensor that is configured to detect light/radiation inside of the disinfection locker detects the presence of light after the emission system should have begun emitting the light/radiation, and advances to step 420, but at step 40 the detected light intensity does not meet a predetermined intensity criteria, process 400 advances to step 435.

At step 435 a notification is sent to a delivery person or to a robot to remove the package from the locker that did not meet criteria and either step 415 or step 420. The notification also indicates to delivery person or to the robot to use a different locker for storing and disinfecting the package and to use a different unlock code corresponding to the different locker. Step 440 a notification is sent to package delivery disinfection server of the need to repair the locker for which the light intensity did not meet predetermined criteria. Step 445 in new locker identification and unlock code is transmitted to the delivery persons UE device or two the robot. At step 450 an out of service message is transmitted to the defective locker. The added service message includes instruction for an indication outside of the locker 2 indicate that the locker is inoperable. For example. If the external indicator is a light capable of displaying different colors the instruction may instruct the light to display a red color. Process 400 advances to step 430 and ends.

Figure 5:
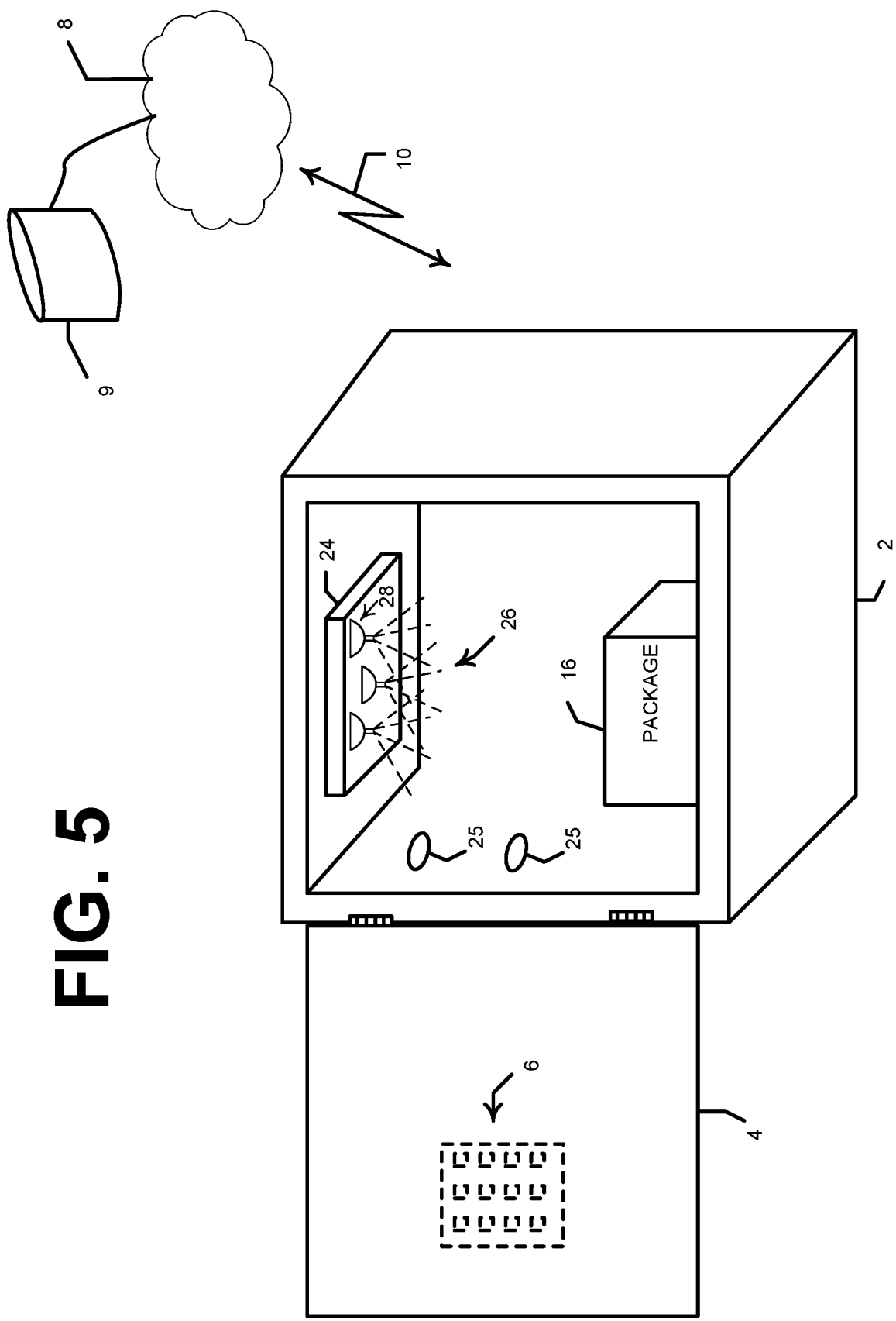
FIG. 5 illustrates a lockable locker with a chemical disinfection system. This diagram also represents a system that may be used for disinfection with nanotechnology material.

Turning now to FIG. 5, the figure illustrates a lockable locker 2. Door 4 is shown in an open position and a backside of keypad 6 is shown. As discussed above in reference to FIG. 1, keypad 6 may include computer circuitry that may further include a data modem for communication via data link 10 and data clout network 8 with server 9. A package 16 is shown having been placed into a cavity of, or container defined by, locker 2. A chemical delivery system 24 is shown with multiple sprays of chemicals 26 emanating from the chemical disinfection dispersing nozzles 28. It will be appreciated that chemical emitting nozzles 28 may be configured to disburse chemicals as liquid, as a gas, as a mist, or as a fog. In an aspect, different types of nozzles may be used to disburse the different forms of the dispersed chemicals. For example, a liquid nozzle may disperse liquid disinfection chemicals when a program running on device 6 server 9, or a delivery person's UE, activates the liquid nozzles. The program may activate different types of nozzles based on the type of packaging used for package 16, or based on the type of contents contained therein. The program may activate misting nozzles that are not the liquid, fogging, or gaseous nozzles based on the type of packaging or contents thereof. The program may activate fogging nozzles that are not the liquid, misting or gaseous nozzles based on the type of packaging or contents thereof. The program may activate gas-disbursing nozzles that are not the liquid, misting, or fogging nozzles based on the type of packaging or contents thereof. Chemical detection sensors 25 may be used in much the same way as light detecting sensors 22 to determine whether disinfection chemicals are being disbursed and whether the chemical is being disbursed at a predetermined rate or intensity to determine whether the chemical system 24 is functioning properly similar to how performance and operability is determined for light or UV intensity at steps 415 and 420 as described in reference to FIG. 4.

Figure 6:
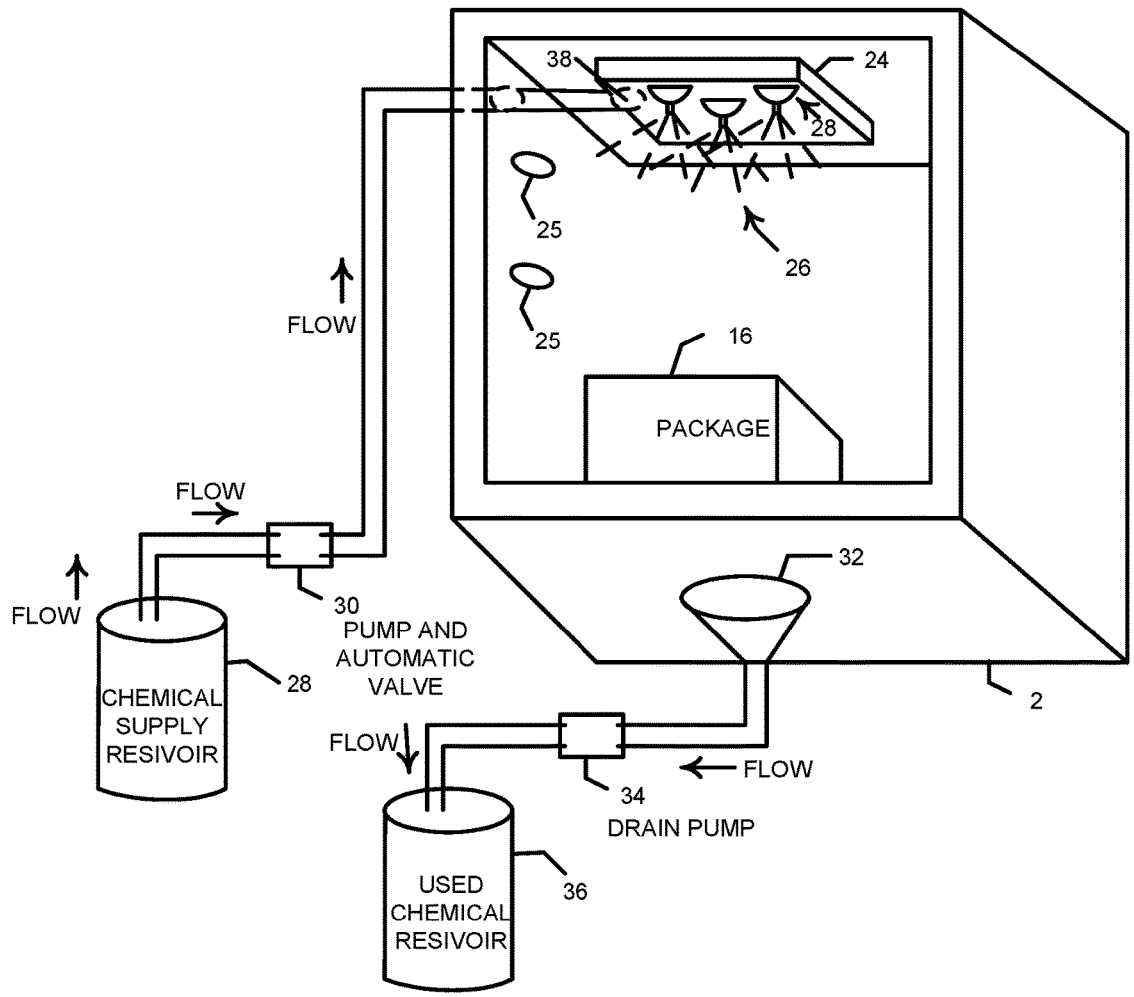
FIG. 6 illustrates supply and drain components of a chemical-based disinfection system. This diagram also represents a system that may be used for disinfection with nanotechnology material.

Turning now to FIG. 6, the figure illustrates supply and drain components of a chemical-based disinfection system. Directions of flow through piping and components are shown in the figure. Chemical supply reservoir 28 contains a disinfection chemical. Supply pump 30, which may include an automatic value that can isolate chemicals of supply tank 28 upon receiving a signal from a controller, such as a keypad computer system of disinfection delivery locker 2, pumps chemical from tank 28 to chemical dispersion nozzles 18. Disinfection chemical contact surfaces of package 16 and collect on the inside bottom of locker 2, where the chemical drains through drain 32. The bottom inside of locker 2 may be configured so that gravity directs or focusses liquid to drain 32. As shown in the figure, drain pump 34 removes liquid from drain 32 and pumps it to used chemical reservoir 36. It will be appreciated that locker 2 and drain components may be configured so that gravity causes chemical at drain 32 to flow to tank 36. However, it will be appreciated that in an aspect tank 36 may be located at a higher elevation than drain 32 and thus pump 34 would be used to pump liquid at drain 32 to tank 36. Similarly, on the supply side, tank 28 may be located at a higher elevation that nozzles 18 such that gravity causes chemical to flow from tank 28 to nozzles without pumping. However, to achieve a desired dispersion pattern and flow rate from nozzles 18 pump 30 may be used to increase pressure of chemical delivered to input port 38 of distribution and disbursing system 24. Distribution system 24 may include pipes or tubes that direct chemical from port 38 to individual nozzles equally and at different rates to different nozzles. The flow rate to individual nozzles may be regulated by valves that correspond to each of nozzles 18. In an aspect, the flow rate to a given one of nozzles 18 may be regulated by a vale corresponding to the nozzle based on a package size or shape value input manually by a delivery user using an application running on his, or her, UE device. Or, sensors placed within locker 2 may detect the size and shape of package 18 and a computer device of the locker, such as, for example, keypad 6 shown and discussed elsewhere herein, may send control signals to individual regulating valves to customize the disinfection chemical discharge/disburse pattern to minimize waste of chemical from tank 28 by minimizing discharge of the disinfection chemical from nozzles that will not impinge more than a predetermined amount on a given side, or surface, or feature, of package 16 based on size, shape, or placement of the packing with locker 2.

It will be appreciated that relative to nanotechnology disinfection material, the systems shown in FIGS. 5 and 6 may be used to disburse nanotechnology material into the inside of locker 2 when its door(s) is/are closed. Nanotechnology material may require different nozzles, or other disbursement means, or different storage tank and plumbing/tubing sizes due to differences in material viscosity or makeup.

Furthermore, it will be appreciated the light/radiation disinfection process 400 described above in reference to FIG. 4 may apply to disinfection using chemical or nanotechnology material. Instead of light/radiation sensors detecting the emission of, and determining the intensity of, light/radiation from light delivery system 18 at steps 415 and 420, respectively, disinfection chemical sensors may similarly detect the discharge of disinfection chemical or nanotechnology material at step 415 and determine the discharge rate thereof at step 420. If the disinfection chemical or nanotechnology material is detected and the discharge rate meets predetermined criteria, the chemical or nanotechnology disinfection process continues and ends after a predetermined period elapses. Similar to the light disinfection process, if sensors do not detect the discharge of disinfection chemical or nanotechnology material, or if the discharge rate does not meet predetermined criteria, the notification sub-process beginning at step 435 begins and a delivery user is advised to remove the package and place in a different locker, for which a new unlock code will be provided to the delivery user. It will be appreciated that sensors may measure flow rate of disinfection chemical or nanotechnology material for individual nozzles. If a given underperforming nozzle has a lower than expected flow rate based on package size, shape and placement, but if the flow rate to another nozzle can be increased to compensate for the reduced flow rate to the underperforming nozzle, the steps beginning at step 435 may not be necessary for the specific package that is currently inside the locker and the disinfection process with the same chemical or nanotechnology may continue with an increased flow rate to other nozzles until complete at step 430. Similarly, if a given underperforming nozzle has a lower than expected flow rate based on package size, shape and placement, but if the flow rate to another nozzle for a different type of disinfection can be used to compensate for the reduced flow rate to the underperforming nozzle, the steps beginning at step 435 may not be necessary for the specific package that is currently inside the locker and the disinfection process with chemical or nanotechnology may continue until complete at step 430. For example, if a chemical fogging nozzle has a reduced flow rate but a nanotechnology material nozzle can supply enough material to the general area that would have been served by the underperforming chemical fogging nozzle, the nanotechnology system may supply nanotechnology material to only the nanotechnology nozzle being called into service to supply disinfection material in place of the underperforming chemical nozzle. Or, if a nanotechnology material nozzle is underperforming, but a light/radiation emitter can compensate for the underperforming nozzle, the light/radiation emitter may be used and the disinfection process may continue until process 400 ends. Or, when a light/radiation emitter is under performing based on light/radiation sensors detecting reduced emitter output, a chemical or nanotechnology nozzle may be pressed into service to compensate. It will be appreciated that an application running on server 9, an application running on a delivery user's UE 12, or a program running on a computer device 6 of the disinfection locker may determine whether a substitute form of disinfection may be used for an underperforming, or nonperforming, radiation emitter, chemical nozzle, or nanotechnology material nozzle and how much flow or radiation intensity to provide to the emitter or nozzle providing back-up disinfection for the underperforming or nonperforming emitter or nozzle. In addition, even though a determination is made that an alternate form of disinfection may be used for a given package size, shape, material, content, or placement within the locker, server 9, or UE device 12 may be notified of the malfunction emitter or nozzle as described in connection with step 440 even though an instruction to remove the package and place it in another locker and a new unlock code is not generated and sent to a delivery user UE.

Figure 7:
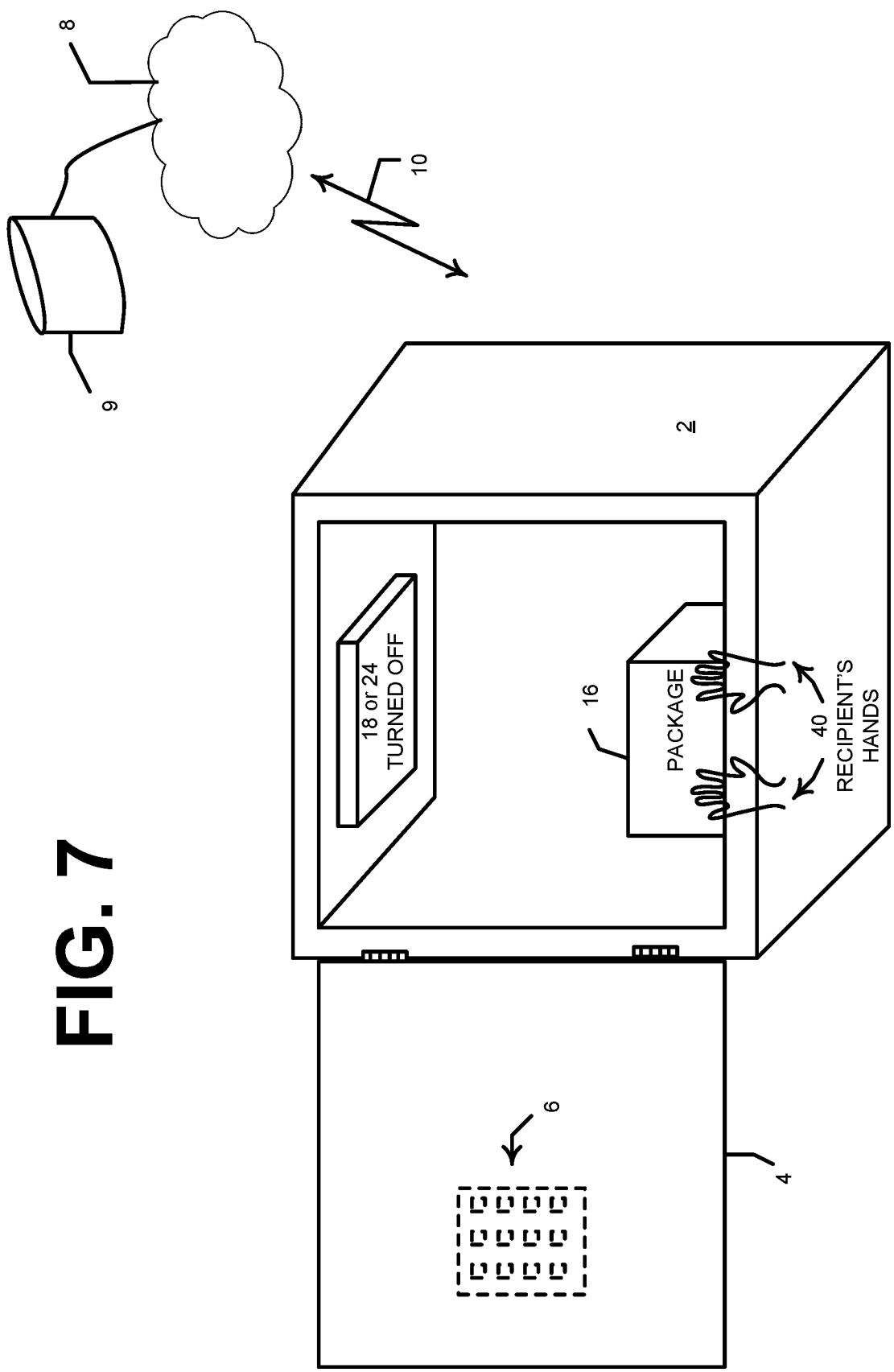
FIG. 7 illustrates a recipient user's hands removing a delivery package from a lockable disinfection delivery locker.

Turning now to FIG. 7, the figure illustrates a recipient user's hand 40 removing package 16 from locker 2 after an indicator on the outside or the locker, or after a notification has been sent to the recipient user's UE device, indicates that disinfection process 400 has completed successfully, that disinfection systems are off (i.e., light/radiation emitters are not emitting or nozzles are not disbursing chemical or nanotechnology material), and that package 16 has been disinfected. It will be appreciated that not only has an indication been generated that indicates to the recipient user that package 16 has been disinfected, but a new unlock code has been sent to the recipient user's UE device in the form of a code for display on the recipient user's UE or in the form of a voice message that communicates the code to the recipient user via the recipient user's UE device. The delivery user, or his or her UE device, does not receive an unlock code to unlock locker 2 after the disinfection process 400 has completed.

Figure 8:
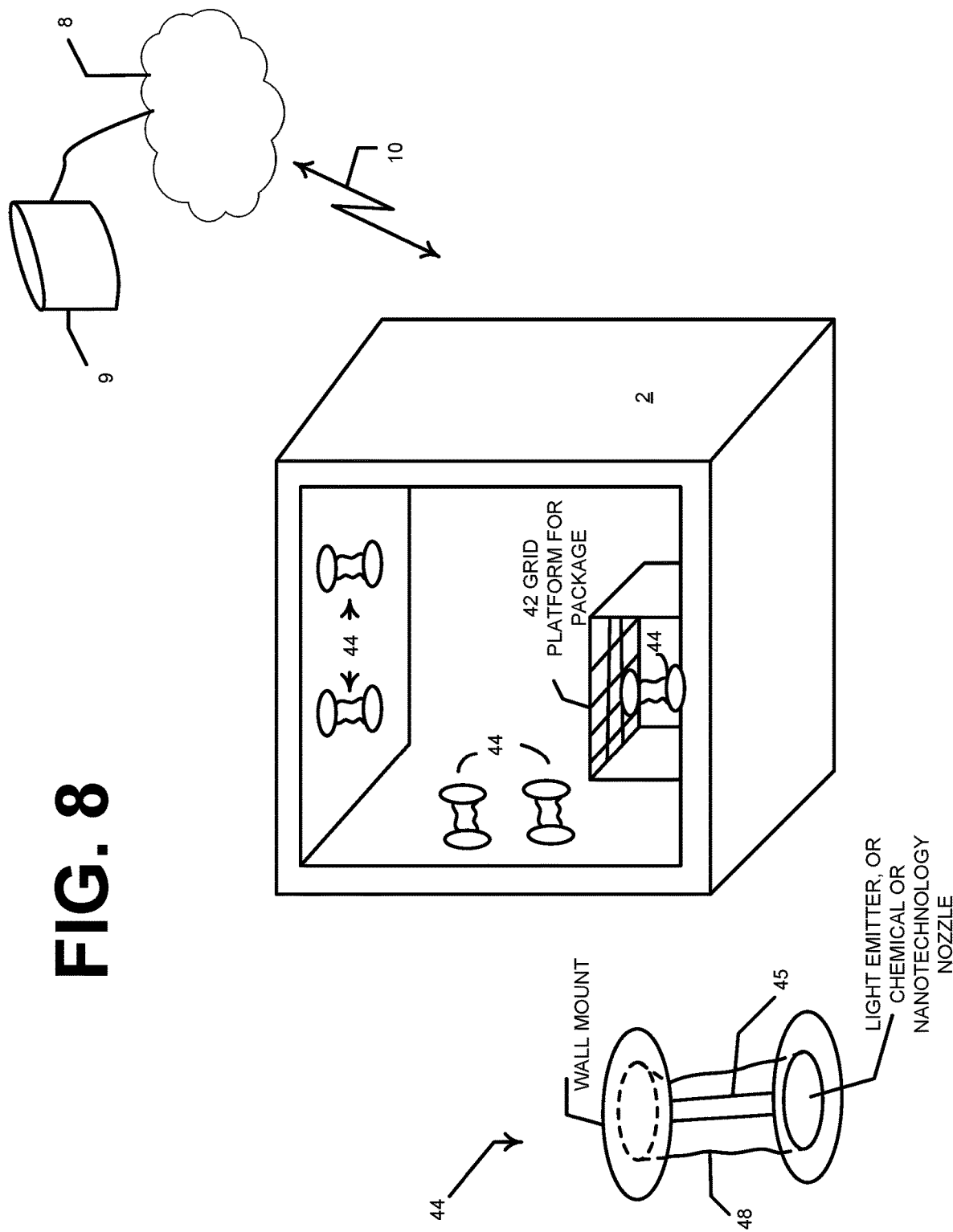
FIG. 8 illustrates a platform for elevating a delivered package relative to flexible infection material delivery components.

Turning now to FIG. 8, the figure illustrates a platform 42 for elevating a package 16 closer to flexible infection material delivery components 44, that may be light/radiation/heat emitters or chemical or nanotechnology nozzles. Platform 42 may comprise a grid made from metal or a composite material that is resistant to the type of disinfection that may take place in a given locker 2. Delivery components 44 may be placed on the end of a flexible adjustable arm, rod, bracket, screw, spring, or similar movable locating means 45 for moving component 44 farther from, or closer to, package 16 that may be located on platform 42. The flexible locating means 45 may be covered by, and removably sealed to the interior of locker 2 by, a flexible material 48, such as a rubber bellows, such that chemical or nanotechnology material may be delivered therethrough to respective components 44. Components 44 (including components that are fixed and not placed on the end of adjustable locating means) may be placed within locker 2 on, or in, sidewalls, the top wall, and bottom wall of the locker. In an aspect, components 44 (including components that are fixed and not placed on the end of adjustable locating means) may be placed in the lockable door of locker 2.

In an aspect a given locker 2 may be configured to deliver some or all of the types of disinfection discussed herein, via radiation emitters and chemical nozzles of various types (fogger, mist, spray, liquid, gas, etc.) and nanotechnology material nozzles of various types (fogger, mist, spray, liquid, gas, etc.) In another aspect, a given locker 2 may be configured to only perform a single type of disinfection and the locker identifier and unlock code sent to a delivery user at step 215 as discussed herein may identify only the type of locker configured to disinfect a given type of package or package contents as may be automatically sensed, previously provided to server 9 from a shipping entity's server that initiates the delivery of the package, or as may be manually specified by a delivery user upon requesting unlock code at step 210 as discussed in reference to FIG. 2 above.

Turning now to FIG. 9, the figure illustrates standoff nozzles 46 used in a disinfection deliver locker 2. The standoff nozzles may be used instead of, or in addition to, platform 42 described above in reference to FIG. 8. The standoff nozzles shown in FIG. 9 are preferably conical shaped to minimize the surface area of package 16 that is blocked from disinfection light, radiation, chemicals, or nanotechnology materials. By placing a package within the locker cavity such that the package rests on tips of the conical nozzles surface area that is not subjected to light, chemical, or nanotechnology material is almost eliminated, and the nozzles are close to the surface of the package to maximize coverage of the light, chemical, or nanotechnology material on the package's surfaces, especially on the bottom surface which may come into contact with more hands and other surfaces that may be contaminated with pathogens as the package moves from the originating shipper to locker 2. In addition to the cone shape that minimizes package surface area shielded from disinfection material, the cones themselves may comprise one or more orifices 49, or nozzles 49, that disperse chemical or nanotechnology material. Standoff nozzles 46 may be adjustable relative to the surface of locker 2 from which they project and may be sealed to walls of the locker with a flexible material 48 to facilitate delivery of disinfection chemicals or nanotechnology material to the standoff nozzles that are adjustable via adjustable locating means 45 as discussed above in reference to the locating means shown in FIG. 8. Nozzles 46 are shown in the figure as fogger nozzles; the nozzles may be configured to disperse chemical or nanotechnology material as a spray, mist, jet, liquid, or other form based on packaging 16 material, package 16 location within the cavity, or contents of the package.

What is claimed is:

1. A system comprising:
   a locker defining a cavity having one or more inner wall surfaces configured to contain delivery packages;
   a lockable door that includes a locking mechanism that unlocks in response to an electronic access request signal, wherein the lockable door provides access to the locker cavity;
   a disinfection system configured to disinfect contents contained in the cavity;
   a computer system that includes a processor to:
   process one or more electronic access request signals;
   evaluate at least one identifier contained in the electronic access request signal to determine whether to provide an unlock message signal to the lockable door based on the evaluated identifier;
   determine whether the evaluation of the identifier contained in the electronic access request signal meets a predetermined unlock criterion, and
   provide an unlock message signal to the lockable door when the identifier contained in the electronic access request signal meets the predetermined unlock criterion;
   wherein the disinfection system subjects contents contained within the cavity to nanotechnology material, via conical nozzles, to kill germs, bacteria, mold, fungus, viruses, or other pathogens, wherein the contents inside the cavity comprise a package resting on tips of the conical nozzles, and wherein the conical nozzles are adapted to disburse the nanotechnology material toward one or more surfaces of the package.

2. The system of claim 1 wherein the processor is further to:
   evaluate the at least one identifier contained in the electronic request signal to determine a type of requestor that requested access to the cavity via the electronic access request signal;

provide a disinfect signal to the disinfection system based on the type of requestor that requested access to the cavity via the electronic access request signal identifier; and wherein the disinfection system performs a disinfection method to disinfect contents in the cavity after receiving the disinfect signal.

3. The system of claim 1 further comprising at least one contents sensor that generates a contents present signal when a delivery package is inside the cavity;

wherein the processor is further to:

receive the contents present signal from the at least one contents sensor;

provide a disinfect signal to the disinfection system based on the receiving of the contents present signal indicating the presence of contents in the cavity; and wherein the disinfection system performs a disinfection method to disinfect contents in the cavity after receiving the disinfect signal.

4. The system of claim 1 wherein the electronic access request signal is transmitted via a cellular wireless signal, a Bluetooth wireless signal, or an internet-based connection by an application program interface running on a cloud-based computer server.

5. The system of claim 1 wherein the electronic access request signal is transmitted via a cellular wireless signal, a Bluetooth wireless signal, from an application program interface running on a delivery user's UE device.

6. The system of claim 1 wherein the disinfection system emits light within the cavity to kill germs, bacteria, mold, fungus, viruses, or other pathogens.

7. The system of claim 1 wherein the disinfection system sprays one or more chemicals into the cavity to kill germs, bacteria, mold, fungus, viruses, or other pathogens.

8. A disinfection locker system service provider server, comprising a processor to:

receive a request from a delivery user to access the inside of an electronically lockable package delivery locker;

generate delivery unlock information;

send the delivery unlock information in a delivery unlock message signal to a UE device of the delivery user;

receive a message from the electronically lockable package delivery locker that the delivery unlock information transmitted in the delivery unlock message signal was used to unlock the lockable package delivery locker;

send a confirmation message to the delivery user's UE that the electronically lockable package delivery locker was unlocked using the delivery unlock information;

receive a message from the electronically lockable package delivery locker that a disinfection system began disinfection inside the electronically lockable package delivery locker;

send a confirmation message to the delivery user's UE that the disinfection began inside the electronically lockable package delivery locker;

receive a message from the electronically lockable package delivery locker that the disinfection inside the electronically lockable package delivery locker completed;

send a message to the delivery user's UE that the disinfection inside the electronically lockable package delivery locker completed; and send a recipient unlock message containing recipient unlock information to a UE of a recipient user but not to the UE of the delivery user, wherein the recipient unlock information is different from the delivery unlock information wherein the disinfecting system comprises conical nozzles to subject contents contained within the electronically lockable package delivery locker to nanotechnology material to kill germs, bacteria, mold, fungus, viruses, or other pathogens, wherein the conical nozzles comprise tips to support the contents inside the lockable package delivery locker, and wherein the conical nozzles are adapted to disburse the nanotechnology material toward one or more surfaces of the contents.

9. The server of claim 8 further comprising receiving a contents-locked message signal that includes information indicating that a door of the lockable package delivery locker has been closed and locked after the message was received from the lockable package delivery locker that the delivery unlock information transmitted in the delivery unlock message signal was used to unlock the lockable package delivery locker and wherein the disinfection system does not begin the disinfection of the inside of the lockable package delivery locker until after the transmitting of the contents-locked message signal by the lockable package delivery locker.

10. The server of claim 8 further comprising transmitting to the lockable package delivery locker disinfection type information based on a type of packaging used for the package, wherein the disinfection type information is intended to be used by the disinfection system to select a type of disinfection to use for disinfecting the package, and wherein the disinfection locker system service provider server contains information that corresponds to the type of packaging used for the package.

11. The system of claim 8 wherein the processor is further to:

generate a content-present signal indicative that contents are not inside the electronically lockable package delivery locker; and responsive to receiving the disinfect signal, disinfect the inside of the electronically lockable package delivery locker when the content-present signal indicates that contents are not present in the cavity.

12. A method, comprising:

unlocking a lockable package delivery locker using recipient unlock information, wherein a disinfection system performs a disinfection process inside the lockable package delivery locker after a delivery user used delivery unlock information to gain access to the inside of the lockable package delivery locker and deliver a package into the lockable package delivery locker and before the recipient unlock information was requested;

wherein the disinfecting system comprises conical nozzles to subject the package to nanotechnology materials to kill germs, bacteria, mold, fungus, viruses, or other pathogens, wherein the conical nozzles comprise tips to support the package, and wherein the conical nozzles are adapted to disburse the nanotechnology materials toward one or more surfaces of the package.

13. The method of claim 12, wherein the recipient unlock information was requested using a UE device of a recipient user.

14. The method of claim 12 wherein the disinfection system is determined from among a plurality of disinfection systems corresponding to the lockable package delivery locker based on package information associated with the package.

15. The method of claim 14 wherein the package information is provided by a disinfection locker system service provider server.

16. The method of claim 14 wherein the package information is provided by a UE device of the delivery user.

17. The method of claim 14 wherein the package information is provided by a computer device of the lockable package delivery locker.

18. The method of claim 17 wherein the computer device of the lockable package delivery locker determines the package information based on package sensor signals sent to the computer device of the lockable package delivery locker from package sensors configured to detect contents of the lockable package delivery locker.

19. The method of claim 17 wherein the computer device of the lockable package delivery locker determines the package information based on package sensor signals sent to the computer device of the lockable package delivery locker from package sensors configured to detect a position of contents of the lockable package delivery locker.

* * * * *